United States Patent
Beauducel et al.

(10) Patent No.: US 7,140,238 B2
(45) Date of Patent: Nov. 28, 2006

(54) METHOD FOR DETERMINING THE COMPOSITION OF A FLUID

(75) Inventors: Claude Beauducel, Henonville (FR); Yohan Bentolila, Paris (FR); Abdelaziz Faraj, Rueil Malmaison (FR); Michel Constant, Montmorency (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 131 days.

(21) Appl. No.: 10/815,676

(22) Filed: Apr. 2, 2004

(65) Prior Publication Data
US 2004/0229376 A1 Nov. 18, 2004

(30) Foreign Application Priority Data
Apr. 4, 2003 (FR) .................. 03 04268
Apr. 4, 2003 (FR) .................. 03 04269

(51) Int. Cl.
*G01N 22/00* (2006.01)
*G01N 33/00* (2006.01)

(52) U.S. Cl. .................. 73/61.41; 73/61.44; 73/61.45; 73/61.49; 73/61.79; 73/599

(58) Field of Classification Search .............. 73/61.41, 73/61.43, 61.44, 61.45, 61.49, 61.79, 584, 73/596, 599
See application file for complete search history.

(56) References Cited

U.S. PATENT DOCUMENTS

| | | | |
|---|---|---|---|
| 4,820,970 A | 4/1989 | Swanson | |
| 4,902,961 A | 2/1990 | De et al. | |
| 5,025,160 A | 6/1991 | Watt | |
| 5,485,743 A | 1/1996 | Taherian et al. | |
| 5,793,216 A | 8/1998 | Constant | |
| 6,277,286 B1 | 8/2001 | Søntvedt et al. | |
| 6,507,401 B1 | 1/2003 | Turner et al. | |
| 2003/0117150 A1 | 6/2003 | Noik et al. | |

FOREIGN PATENT DOCUMENTS

| | | |
|---|---|---|
| EP | 0 499 424 A2 | 8/1992 |
| EP | 0 733 780 A1 | 9/1996 |
| EP | 0 783 102 A1 | 7/1997 |
| GB | 2 294 074 A | 4/1996 |
| WO | WO 91/05243 | 4/1991 |
| WO | WO 00/22387 | 4/2000 |
| WO | WO 01/36951 A2 | 5/2001 |
| WO | WO 03/012378 A1 | 2/2003 |

*Primary Examiner*—Daniel S. Larkin
(74) *Attorney, Agent, or Firm*—Antonelli, Terry, Stout and Kraus, LLP.

(57) ABSTRACT

Method for determining the composition of a homogeneous fluid, for example a petroleum effluent on flow, an emulsion consisting of water and oil, or a foam consisting of oil and gas.

The attenuation and the phase shift of microwave beams that have traversed a fluid of unknown composition with paths of different lengths are measured (stage A). Two equations approaching the measured values are determined, the first equation giving a relation between the attenuation and the length of the path, the second equation giving a relation between the phase shift and the length of the path (stage C). Then the composition of the fluid is determined by comparing the two equations with pairs of equations stored in form of databases, each pair of equations corresponding to a fluid of known composition (stage D).

19 Claims, 4 Drawing Sheets

METHOD FOR DETERMINING THE COMPOSITION OF A FLUID

FIELD OF THE INVENTION

The present invention relates to a method for determining the composition of a fluid. More precisely, the invention provides a data processing method analysing characteristics of microwave beams that have traversed a fluid in order to determine the composition of this fluid.

The method according to the invention is particularly well-suited for determination of the composition of multiphase fluids comprising for example water, oil and/or gas. For example, the method can apply to determination of the composition of a petroleum effluent contained in a separating drum or flowing in a line.

The method can also apply to a heterogeneous fluid. For example, the method according to the invention is suited to determine the position and the composition of several superposed fluid layers. For example, the method can apply to a petroleum effluent contained in a separating drum or flowing in a line. Depending on the conditions of use of this effluent, for example under the effect of gravity, the different phases of the effluent (water, oil and gas) are distributed in stratified form, i.e. in several superposed layers of distinct and homogeneous compositions. The method allows to determine the position of the layers of water, oil, gas, emulsion consisting of water, oil and gas, and foam consisting of oil and gas, etc. Furthermore, the method allows to determine the composition of single-phase layers of emulsion and foam.

BACKGROUND OF THE INVENTION

Document FR-2,833,705 provides a separating drum comprising a first rod fitted with microwave beam emitters, a second rod fitted with microwave beam receivers. The separator contains a petroleum effluent from a production well. A microwave source is connected to the emitters so that each emitter can emit a microwave beam. An acquisition device records the microwave beams picked up by the receivers and the microwave beam emitted by the source.

The present invention provides a method of processing the characteristics of the microwave beams picked up by the receivers in order to determine the composition of the fluid traversed by these beams.

SUMMARY OF THE INVENTION

In general terms, the present invention relates to a method for determining the composition of a substantially homogeneous fluid, wherein the following stages are carried out:

a) measuring the attenuation and the phase shift of at least two wave beams that have travelled paths of different distances in said fluid, b) determining relations modelling the variations of the attenuation and phase shift of the waves as a function of the distance, measured in stage a), c) determining the composition of the fluid by comparing the relations determined in stage b) with a set of previously determined relations, each relation of said set corresponding to a fluid of known composition.

According to the invention, in stage a), at least two of said wave beams may have travelled two different paths of equal distance in said fluid and a mean, for example weighted, of the attenuations and of the phase shift measured for said at least two beams that have travelled two different paths of equal distance in said fluid can be worked out.

According to the invention, in stage c), the set of previously determined relations can be obtained by carrying out stages a) and b) on fluids of known composition.

According to the invention, in stage b), a first equation of the attenuation as a function of the distance and a second equation of the phase shift as a function of the distance can be determined, the first and second equations approaching the attenuation and phase shift measurements of stage a), and in stage c), the composition of the fluid can be determined by comparing the first and second equations determined in stage b) with pairs of previously determined equations, each pair of equations corresponding to a fluid of known composition.

The first equation can be of the form $\rho=e^{-\alpha\theta-\alpha_0}$, the second equation can be of the form $\theta=\lambda d+\lambda_0$, $\rho$ being the attenuation, $\theta$ being the phase shift, $\alpha$, $\alpha_0$, $\lambda$ and $\lambda_0$ being constants, and the values of constants $\alpha$, $\alpha_0$, $\lambda$ and $\lambda_0$ are determined. In stage c), the values of the constants determined in stage b) can be compared with groups of previously determined constants, each group of constants corresponding to a fluid of known composition, said groups of previously determined constants being obtained by carrying out stages a) and b) on fluids of known composition. In stage b), a linear regression can be used to determine the values of the constants.

According to the invention, in stage c), the pressure of said fluid, the temperature of said fluid and/or the salinity of said fluid can be taken into account.

According to the invention, in stage c), the composition of the fluid can be determined by selecting in the set of previously determined relations the relations that best match the relations obtained in stage b).

According to the invention, in stage c), a model allowing to assign a known composition to relations modelling the attenuation and phase shift variations as a function of the distance can be used, the model being constructed by means of the set of previously determined relations. The model can be a statistical model or a behavioural model, the model being a polynomial function or a neural network.

According to the invention, the waves can be microwaves.

A variant of the present invention relates to a method for determining the composition of a fluid contained in a volume, said fluid comprising at least two phases in stratified layers, wherein the following stages are carried out:

a) defining several sections that divide said volume, each section comprising a part of said fluid, b) measuring the attenuation and the phase shift of a microwave beam that has travelled a path in a first one of said sections, c) determining the composition of the part of said fluid located in said first section by comparing the attenuation and the phase shift measured in stage b) with a set of pairs of previously determined attenuation and phase shift values, each pair of said set characterizing a fluid of known composition, d) repeating stages b) and c) for each section defined in stage a), e) determining the position of said layers from the compositions determined in stage c) and from the definition of the sections in stage a), f) measuring the attenuation and the phase shift of at least two wave beams that have travelled paths of different distances in a first one of said layers, g) determining relations modelling the wave attenuation and phase shift variations as a function of the distance, measured in stage f), h) determining the composition of the fluid forming the first layer by comparing the relations determined in stage g) with a set of previously determined relations, each relation of said set corresponding to a fluid of known composition.

According to the variant of the invention, the sections defined in stage a) can be superposed and separated by parallel planes.

In stage c), at least one of the following conditions can be taken into account: pressure, temperature and salinity of said fluid.

In stage c), a model allowing to assign a composition to a family of values measured in stage b) can be used, the model being constructed from said set of families of values. It is possible to use a statistical model or a behavioural model, of linear, quadratic and neural network type, and a regression of linear, PLS or neural network type is used.

In cases where the fluid is a petroleum effluent comprising water, oil and gas, the model can carry out operation 1: the family of values is classified by discriminant analysis in one of the following categories: water single-phase, oil single-phase, gas single-phase or multiphase, if the family of values is classified in a single-phase category, then the composition of the effluent is determined, if the family of values is classified in the multiphase category, operations 2 and 3 are carried out:

Operation 2: the family of values is classified in a subcategory corresponding to a fluid comprising a phase in a proportion contained in a fixed interval within [0%; 100%].

Operation 3: the proportion of the phase corresponding to the subcategory is determined by regression on the fixed interval.

BRIEF DESCRIPTION OF THE FIGURES

Other features and advantages of the invention will be clear from reading the description hereafter, given by way of example, with reference to the accompanying drawings wherein.

DETAILED DESCRIPTION

Figure 1:
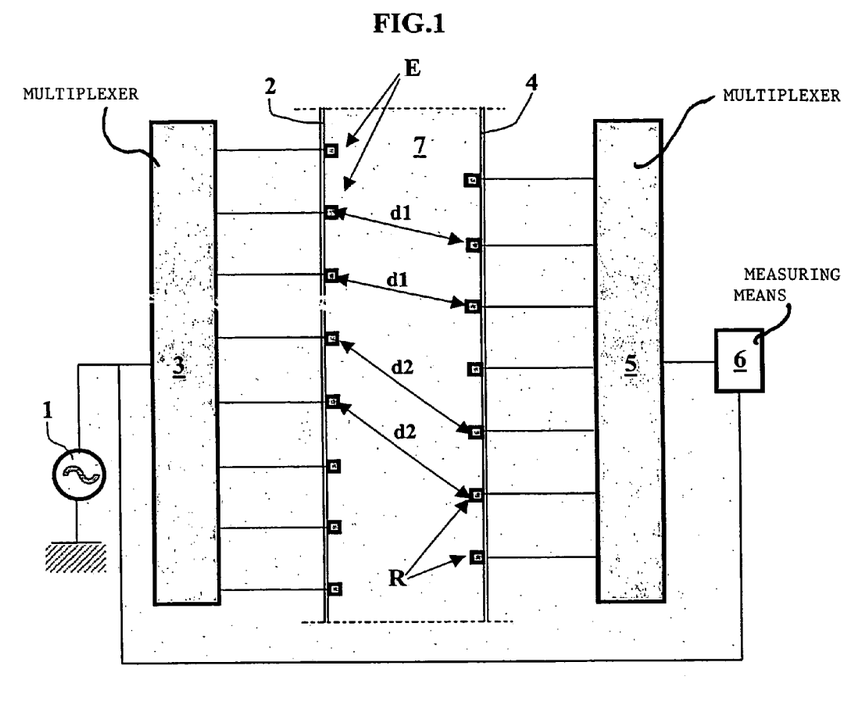
FIGS. 1 and 7 diagrammatically show the measuring device.

The method according to the invention can exploit the measurements obtained by means of the measuring device diagrammatically shown in FIG. 1. The measuring device comprises a microwave beam source 1 connected to microwave emitters E arranged on first line 2. The frequency of the microwave beam emitted by source 1 can be selected and modified. Microwave beam receivers R arranged on second line 4 are connected to measuring means 6. A fluid 7 whose composition is to be determined, a petroleum effluent for example, is in position in the space located between first line 2 and second line 4. A multiplexer 3 allows to connect source 1 to any emitter E. Thus, the emitter which is connected to source 1 emits a microwave beam that is propagated in fluid 7. The microwave beams are considered to be propagated in straight lines in fluid 7. Multiplexer 5 allows to connect any receiver R to measuring means 6. Measuring means 6 are also connected to source 1. Thus, measuring means 6 can record the characteristics of the microwave beam picked up by the receiver that is connected to measuring means 6 as well as the characteristics of the microwave beam directly emitted by source 1.

The emitters and receivers can be on first and second lines 2 and 4 so as to have one or more emitter-receiver pairs separated by the same first distance d1 and one or more emitter-receiver pairs separated by the same second distance d2. In general, there are at least two emitter-receiver pairs separated by at least two different distances.

Lines 2 and 4 can have the shape of curves, the shape of straight lines, parallel or not. The emitters can be arranged at regular intervals on first line 2 (i.e. the value of the distance between two adjacent emitters is identical for all the emitters) and/or the receivers can be arranged at regular intervals on second line 4 (i.e. the value of the distance between two adjacent receivers is identical for all the receivers). When the emitters and the receivers are arranged at regular intervals on lines 2 and 4, the value of the interval between two adjacent emitters can be equal to or be a whole multiple of the value of the interval between two adjacent receivers.

Lines 2 and 4 can be located on the walls of a vessel containing fluid 7, for example on the wall of a pipe carrying fluid 7. Lines 2 and 4 can also be arranged on rods that plunge into fluid 7 contained in a vessel, for example a separating drum used in the petroleum industry.

Emitters E and receivers R are antennas known to the man skilled in the art, for example described in connection with FIG. 2 of document FR-2,833,705.

Without departing from the scope of the invention, the type of wave produced by source 1 can also be selected from among electromagnetic radiation waves such as microwaves, infrared, nuclear radiation, optical light, or from among acoustic waves such as ultrasounds.

Fluid 7 can be a single-phase fluid, i.e. consisting of one or more constituents that mix. Fluid 7 can also be a multiphase fluid, i.e. consisting of several constituents that do not mix. The method according to the invention is well-suited for determination of the composition of a homogeneous fluid, i.e. a fluid whose composition is substantially identical for any part of the fluid or, expressed differently, the constituents of the fluid are distributed in a substantially identical manner in all of the fluid.

For example, fluid 7 can be a petroleum effluent comprising water, oil and/or gas.

Figure 2:
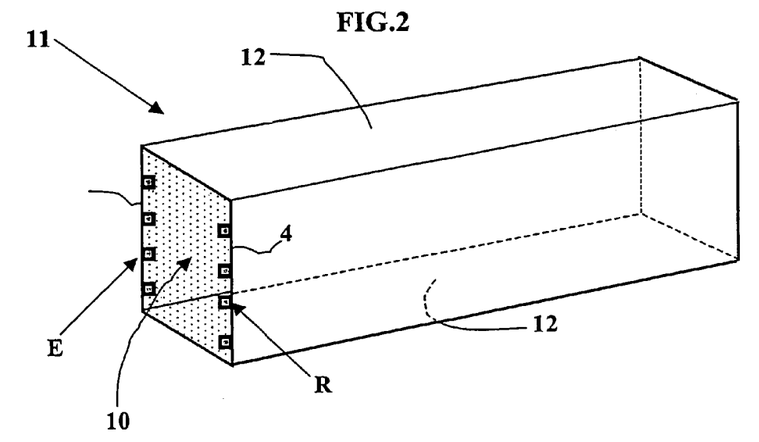
FIGS. 2 and 3 show two examples of fluids to which the method according to the invention can be applied.

With reference to FIG. 2, petroleum effluent 10 can be on turbulent flow in a pipe 11. In this case, the composition of the effluent can be homogeneous, i.e. the water, the oil and the gas are distributed uniformly in all of pipe 11. In this case, the method allows one to determine the water, oil and gas content of the effluent.

Figure 3:
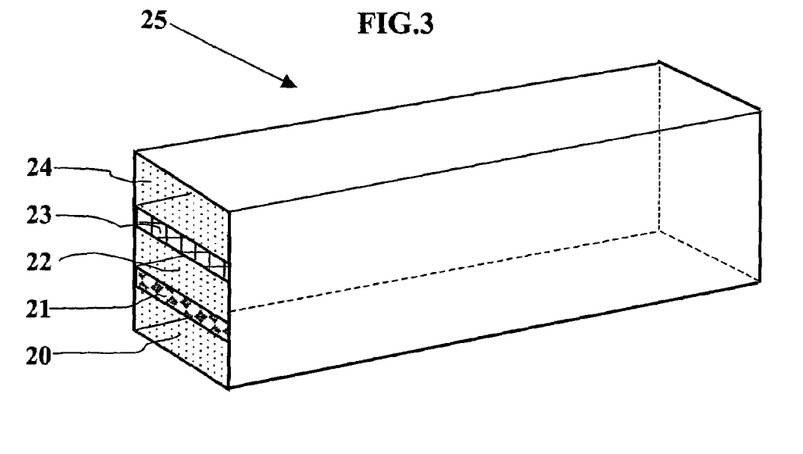

According to another option diagrammatically shown in FIG. 3, the water 20, the oil 22 and the gas 24 can be distributed in form of stratified layers, for example when the effluent is on laminar flow in a pipe 25 or when the effluent settles in a separating drum. More precisely, the effluent comes in form of superposed layers: a water layer 20, a water/oil emulsion layer 21, an oil layer 22, an oil/gas foam layer 23 and a gas layer 24. In this case, the method notably allows one to determine the position of the various layers and to determine the proportions of water and oil forming emulsion layer 21, and the proportions of oil and gas forming foam layer 23. To determine the composition of the emulsion (respectively of the foam), only the microwave beams that have travelled a path located only in emulsion layer 21 (respectively in foam layer 23) are taken into account.

Figure 4:
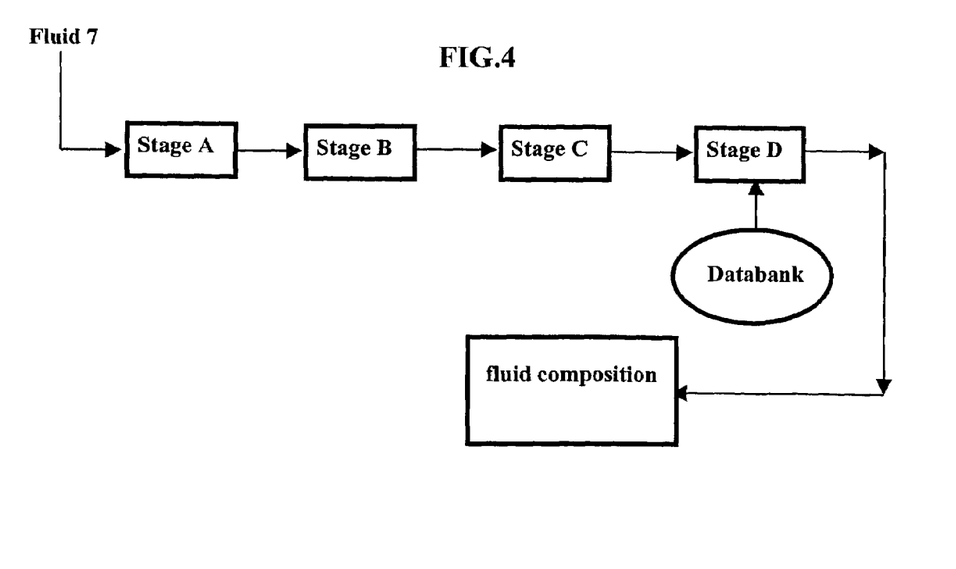
FIG. 4 is a diagram of the method according to the invention.

The method according to the invention is described in connection with the diagram of FIG. 4.

Stage A: Measurements

The measuring device described in connection with FIG. 1 works by double emission and reception multiplexing. Microwave source 1 produces a microwave beam of selected frequency f1. Multiplexer 3 connects microwave source 1 successively to each emitter E. Thus, the emitters emit one after the other a microwave beam. During the emission time of one emitter E, multiplexer 5 connects successively or simultaneously each receiver R to measuring means 6. Measuring means 6 also measure the microwave beam emitted by source 1. Thus, measuring means 6 measure the characteristics of the microwave beam emitted by an emitter and picked up by each receiver. It is thus possible to measure the microwave beam emitted by an emitter and picked up by a receiver, for all the emitter-receiver pairs available.

Frequency f1 can be selected so that the microwave beam is substantially modified by at least one of the constituents of fluid 7 when the beam is propagated in fluid 7, i.e. the attenuation and the phase shift are appreciable when the beam is propagated in fluid 7. For example, frequency f1 is so selected that the microwave beam is substantially modified when it traverses natural gas ($CH_4$). Thus, by measuring the attenuation and the phase shift of a beam of frequency f1 that has traversed a petroleum effluent, information on the natural gas content of this effluent is obtained.

The measurements can be repeated for several microwave beam frequencies. The frequencies can be so selected that, for each frequency, the microwave beam is substantially modified by a constituent of the fluid and, for each different frequency, the beam is substantially modified by a different constituent. For a petroleum fluid containing water, oil and/or gas, the frequencies can be selected between 1 GHz and 100 GHz, preferably between 2 GHz and 10 GHz, for example the four frequencies contained in the following intervals:

Fa [2 GHz; 2.7 GHz]
fb [2.7 GHz; 3.7 GHz]
fc [3.7 GHz; 6 GHz]
fd [6 GHz; 10 GHz].

Stage B: Measurement Processing

The attenuation and the phase shift of the beam that has traversed the fluid over the distance separating an emitter E and a receiver R are determined knowing the characteristics of the microwave beam emitted by this emitter (i.e. the beam emitted by source 1) and the characteristics of the microwave beam picked up by this receiver.

For example, the attenuation and phase shift values can be classified in a matrix of complex numbers whose component Mij corresponds to the attenuation and phase shift values of the beam of frequency f1 emitted by emitter i and picked up by receiver j. When the measuring device comprises n emitters and m receivers, the matrix is of dimension n×m. By carrying out the measurements for the four frequencies fa, fb, fc and fd, four matrices are obtained, each one corresponding to measurements performed at one of the four frequencies.

When the receivers and the emitters are arranged on two straight and parallel lines, at regular and equal intervals, the values located on the same diagonal of the matrix correspond to the attenuation and phase shift values of the beams that have travelled paths of equal distance between emitters and receivers. Thus, the measurements corresponding to microwave beams that have travelled paths of equal distance in the fluid are located on the same diagonal of the matrix.

In order to obtain a more reliable value for the attenuation and phase shift values, the mean of the measured attenuations and phase shifts corresponding to beams that have travelled paths of equal distance in the fluid can be worked out. Thus, the taking account of phenomena that may occur in isolation during a measurement and distort this measurement can be limited. A single phase shift and attenuation value corresponding to the beams that have travelled a determined distance is obtained.

When the measurements are classified in a matrix, a mean of the measurements of each diagonal is worked out, i.e. of the attenuation and phase shift measurements that correspond to the same distance travelled by the microwave beams. Thus, instead of analysing n×m complex values, the number of values to be analysed is reduced to the greater one of numbers n and m.

A weighted mean of the values can be worked out. It is thus possible for example to minimize the edge effects notably due to the reflection of the microwave beams and to homogeneity variations of fluid 7.

In fact, with reference to FIG. 2, the emitters E and the receivers R located at the ends of lines 2 and 4 can be close to walls 12 of the pipe or of the vessel containing fluid 10. The composition of fluid 10 can be modified in the area surrounding walls 12, for example because of the flow of fluid 10 that is disturbed by the presence of walls 12. Thus, the attenuation and the phase shift of the microwave beams that traverse these fluid portions in the area around walls 12 are not representative of all of the composition of fluid 10.

Furthermore, microwave beams are reflected on walls 12 of the pipe or of the vessel containing fluid 10. The receivers R located close to walls 12 can record these reflected beams. Thus, the attenuation and the phase shift determined from the microwave beam emitted by an emitter and the microwave beams measured by an emitter located close to a wall 12 may not be representative of the attenuation and of the phase shift of the beam propagated rectilinearly from this emitter to this receiver.

Consequently, by working out a weighted mean of the measurements, it is possible to give less weight to the attenuation and phase shift values measured close to walls 12. These attenuation and phase shift values will thus be less important in relation to the other values during the later stages of the method according to the invention.

Stage C: Converting Measurements to Equations

A matrix grouping together the attenuation and phase shift values measured for a microwave beam frequency is a way of characterizing fluid 7. However, this matrix is difficult to use because it groups a large number of values.

The present invention proposes to convert this matrix grouping together a set of values into information that can be processed more readily. The phase shift and attenuation values matrix is converted into two equations:

a first equation f giving a mathematical relation between the attenuation ρ of a microwave beam and the distance d of the path travelled by this beam in fluid 7: $\rho = f(d)$ a second equation g giving a mathematical relation between the phase shift θ of a microwave beam and the distance d of the path travelled by this beam in fluid 7: $\theta = g(d)$.

Equation f, respectively g, is determined so as to approach the attenuation values ρ, respectively the phase shift values θ, of a microwave beam, measured for several values of the distance travelled by this microwave beam in the fluid of unknown composition.

Determination of equations f and g can be carried out as follows.

For each equation f and g, a general mathematical expression is selected. The general expression comprises at least two unknown constants.

Advantageously, general expressions related to the physical phenomena observed during the attenuation and phase shift measurements can be selected. It is known from physical theories that attenuation of a microwave beam varies exponentially as a function of the distance of the path travelled by this beam in a fluid and that the phase shift varies linearly as a function of this distance.

For example, the following general expressions can be selected for equations f and g:
for function f: $\rho = e^{-\sigma d - \sigma_0}$
for function g: $\theta = \lambda d + \lambda_0$ with d: distance travelled by the microwave beam in the fluid, and $\lambda$, $\lambda_0$, $\sigma$ and $\sigma_0$: unknown constants.

Without departing from the scope of the invention, other general expressions can be selected for equations f and g, comprising for example more than two constants each. Furthermore, equations f and g can be a function of a variable other than the distance. However, this other variable depends itself on the distance. The following expressions can be selected for example:
for function f: $\rho = e^{-\sigma \theta - \sigma_0}$
for function g: $\theta = \lambda d + \lambda_0$ with d: distance travelled by the microwave beam in the fluid, and $\lambda$, $\lambda_0$, $\sigma$ and $\sigma_0$: unknown constants.

Phase shift $\theta$ being a function of distance d, attenuation $\rho$ can be expressed as a function of phase shift $\theta$.

After selecting the general mathematical expressions for equations f and g, the constants of these equations are determined. Using methods known to the man skilled in the art such as linear regression, the constants of equations f and g are determined so that equations f and g approach the measured attenuation $\rho$ and phase shift $\theta$ values.

Figure 5:
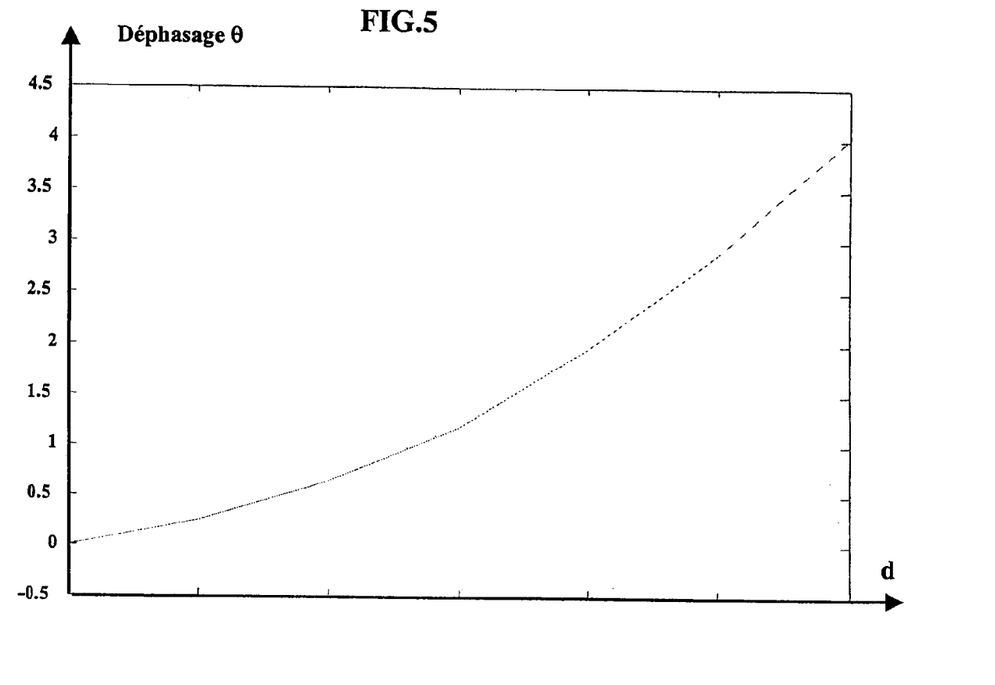
FIG. 5 shows the phase shift measurements as a function of the distance.

FIG. 5 shows the phase shift values $\theta$ as a function of distance d. Each point of the curve corresponds to the attenuation measured for a distance travelled by the microwave beam in the fluid of unknown composition. Thus, this curve can be approached by a straight line, which can be written $\theta = \lambda d + \lambda_0$, by determining constants $\lambda$ and $\lambda_0$.

Figure 6:
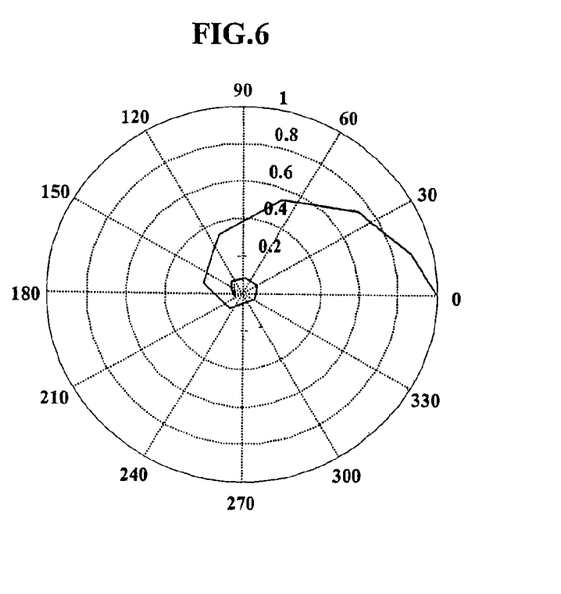
FIG. 6 shows the attenuation measurements as a function of the phase shift in a complex plane.

FIG. 6 shows the attenuation values $\rho$ as a function of phase shift $\theta$ in polar coordinates in a complex plane, $\rho$ being the radius and $\theta$ the angle. Each point of the curve corresponds to the attenuation and to the phase shift measured for a distance travelled by the microwave beam in the fluid. Thus, this "wheeling" curve can be approached by a logarithmic spiral, that can be written in the form: $\rho = e^{-\alpha \theta - \alpha_0}$, by determining constants $\alpha$ and $\alpha_0$.

Thus, for a microwave beam frequency, from a matrix grouping n×m attenuation and phase shift values that characterize fluid 7, we obtain two equations that characterize fluid 7. These two equations can be characterized by a group of at least four coefficients.

An offset of the measured curve shown in FIG. 6 may appear in relation to the origin of the complex plane. This offset can be due to too high a salinity of fluid 7, which consequently causes a greater dispersion of the microwave beams and generates an electronic offset. It is possible to remove this offset by means of electronic adjustments on measuring means 6.

Stage D: Fluid Composition Estimation

Besides, a databank grouping together pairs of equations f and g has been created, each pair of equations f and g characterizing a fluid of known composition. The equation pairs of the databank can be obtained by carrying out stages A, B and C described above, i.e. each pair of equations f and g of the databank approaches the curves obtained by the attenuation and phase shift measurements of a microwave beam traversing a fluid of known composition as a function of the distance travelled by the beam in this fluid, the microwave beam being of known frequency. The frequencies of the microwave beams used to create the databank are identical to the frequency of the microwave beams used in stage A.

Equations f and g of the databank can be characterized by constants. Each equation pair of the databank can be characterized by at least four constants. In this case, the general mathematical expressions of equations f and g used to create the databank are identical to the general mathematical expressions used during processing of the attenuation and phase shift measurements performed on a fluid of unknown composition.

Thus, each pair of equations f and g of the databank characterizes a fluid of known composition.

According to the invention, equations f and g obtained in stage C by processing the attenuation and phase shift measurements on a fluid of unknown composition are compared with the pairs of equations f and g of the databank so as to determine the composition of the fluid studied. The comparison takes account of the microwave beam frequency used during measurement.

To make the comparison, a model can be constructed from the pairs of functions of the database, the model allowing to assign a known fluid composition to a pair of equations. A statistical or a behavioural model can be used. The models used can be polynomial functions or neural networks.

It is possible, for example, to compare the constants characterizing equations f and g obtained in stage C by processing the attenuation and phase shift measurements on a fluid of unknown composition with the constants characterizing the pairs of equations f and g of the databank. To make the comparison, a model can be constructed from the groups of constants of the database, the model allowing to assign a known fluid composition to a group of constants.

To make the comparison, it is also possible to select in the database the pair or pairs of equations that best match equations f and g obtained in stage C and to determine the composition of the fluid from the compositions corresponding to the pair or pairs of equations selected.

Furthermore, to improve the accuracy of estimation of the composition of fluid 7, the salinity, the pressure and/or the temperature of fluid 7 can notably be taken into account. The salinity, the pressure and the temperature can be measured by detectors arranged in fluid 7.

In this case, the databank also comprises the salinity, pressure and/or temperature values: the equation pairs of the databank characterize a known fluid at a known temperature, pressure and/or salinity. It is thus possible to make the comparison between the equation pairs obtained by measurement and the equation pairs of the databank by taking account of the salinity, the pressure and/or the temperature.

The composition of the fluid studied can for example be determined by making the comparison between, on the one hand, the values of the constants characterizing equations f and g, salinity pressure and/or temperature values, these values being determined from the attenuation and phase shift measurements of microwave beams that have traversed the fluid of unknown composition, with the sets of values of the constants characterizing equations f and g, and salinity, pressure and/or temperature values from the database.

In the case of a fluid comprising several stratified layers, for example a fluid as shown in FIG. 3, the method according to the invention can be completed by stages E, F and G. These stages allow to determine the position of the stratified layers. Stages E, F and G are carried out prior to stage B, with data measured in stage A.

Stage E: Data Structure

The modifications of the wave beam that has traversed the fluid over the distance between an emitter E and a receiver R are determined knowing the characteristics of the wave beam emitted by this emitter (i.e. the beam emitted by source 1) and the characteristics of the wave beam picked up by this receiver. These modifications are quantified by a family of values, for example by the attenuation, the phase shift, the direction or the polarization of the wave that has traversed the fluid. For example, the attenuation and the phase shift of a microwave beam that has traversed the fluid over the distance between an emitter E and a receiver R are determined knowing the characteristics of the microwave beam emitted by this emitter (i.e. the beam emitted by source 1) and the characteristics of the microwave beam picked up by this receiver.

For example, the attenuation and phase shift values can be classified in a matrix of complex numbers whose component Mij corresponds to the attenuation and phase shift values of the beam of frequency f1 emitted by emitter i and picked up by receiver j. When the measuring device comprises n emitters and m receivers, the matrix is of dimension n×m. By performing the measurements for the four frequencies fa, fb, fc and fd, four matrices are obtained, each one corresponding to measurements performed at each one of the four frequencies.

When the receivers and the emitters are arranged on two straight and parallel lines at regular and equal intervals, the values located on the same diagonal of the matrix correspond to the attenuation and phase shift values of the beams that have travelled a path between an emitter and a receiver separated by the same distance. Thus, the corresponding measurements of the wave beams that have travelled the same distance in the fluid are located on the same diagonal of the matrix.

Stage F: Fluid Composition Determination

Figure 7:
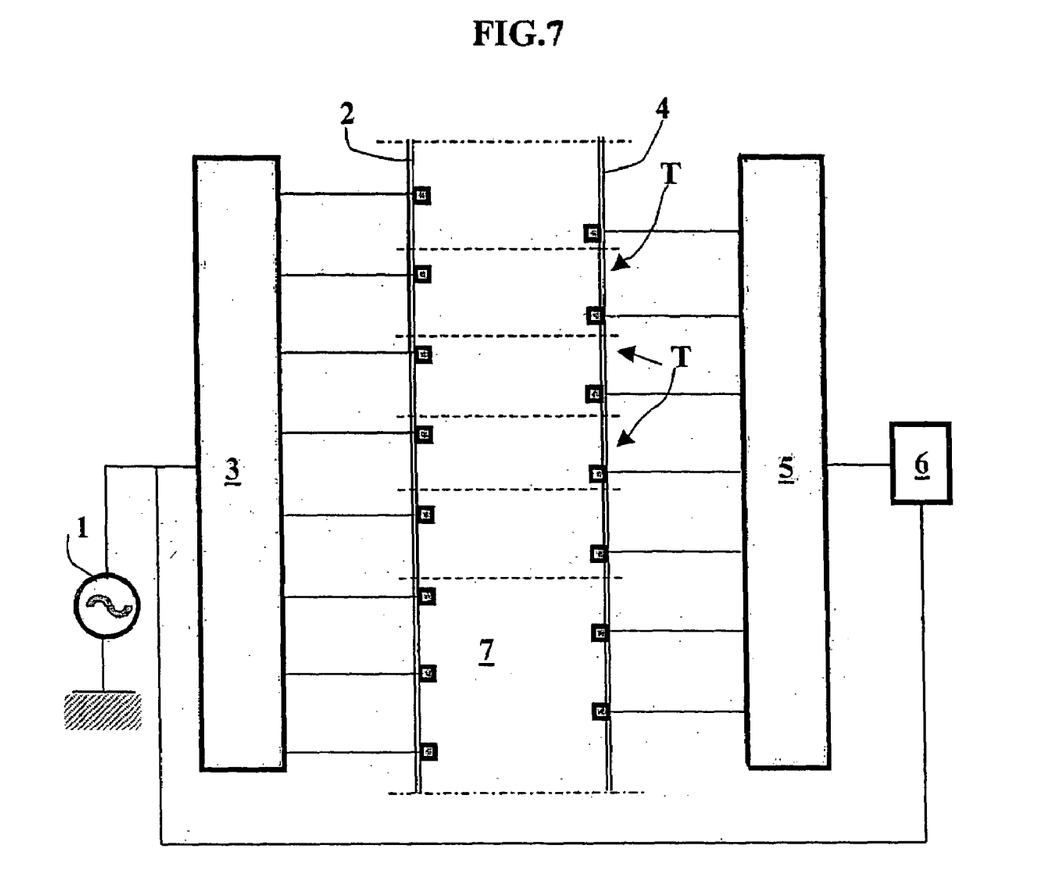

To construct a mapping of fluid 7, the volume in which the fluid is located, i.e. the space contained between lines 2 and 4, is split into sections T. FIG. 7 shows the measuring device of FIG. 1 in which the fluid is split into sections T. Each section T can be defined by the volume located between two surfaces, for example between two planes, two parallel planes or two horizontal planes. In FIG. 7, sections T consist of volumes located between horizontal planes, the sections being superposed. In this case, the sections can be of constant or variable thickness. Sections T can be so selected that a section T comprises at least one emitter E and at least one receiver R arranged on lines 2 and 4. In section T, the emitter and the receiver can be positioned at any point respectively on lines 2 and 4. For example, emitter E, respectively receiver R, can be arranged on line 2, respectively on line 4, on one of the boundary surfaces of section T. The distance between the emitter and the receiver is known.

Furthermore, a base consisting of experimental data of the possible configurations of fluid 7 (for example single-phase, multiphase, stratified, dispersed, emulsified, . . . ) and of experimental configurations (for example pressure, temperature, salinity, etc.) has been created, the composition of fluid 7 being known. Each experiment involves measurements associated with the configuration of fluid 7, the experimental conditions and the modifications of the wave beams that have traversed the fluid. The wave beam modifications and the experimental conditions are characterized by a family of values which comprises, for example, the attenuation, phase shift, temperature, pressure and salinity values. Thus, the databank groups together, for each experiment carried out on a fluid of known composition, the measurements of the experimental configurations and the values representing the modifications of the wave beams that have traversed the fluid. The values used can be direct values and/or combinations of direct values (by multiplication, by trigonometric, logarithmic, exponential transformations, etc.).

This family of values will be used later at the input of the model described hereafter to determine the fluid type (single-phase, emulsified, . . . ) and the proportions of each phase forming the fluid.

A model allowing to assign a known composition to a family of values is constructed from the databank, i.e. when a family of values is entered in the model, it responds by giving the type and the composition of the fluid. The model is constructed using methods known to the man skilled in the art, such as a statistical or behavioural model using a polynomial function, a neural network or a discriminant analysis.

Thus, the composition of the fluid located in a section T is determined using the model constructed beforehand from the database: the model determines the composition of the fluid from the family of values representing the modifications of the wave beam that has traversed the fluid of unknown composition in this section T.

Furthermore, to improve the accuracy of estimation of the composition, the salinity, the pressure and/or the temperature of the fluid of unknown composition can notably be taken into account. The salinity, the pressure and the temperature can be measured by detectors arranged in the fluid.

In this case, the database also comprises the salinity, pressure and/or temperature values: each family of values of the databank characterizes a known fluid at a known salinity, pressure and/or temperature.

The model constructed from the database also takes account of the salinity, pressure and/or temperature values. Thus, the model allows to assign a fluid composition to a family of values representing the modifications of the wave beam that has traversed the fluid of unknown composition, completed with the salinity, pressure and/or temperature values of this fluid of unknown composition. In other words, by giving a family of values and the salinity, pressure and/or temperature values to the model, it responds by giving a fluid composition.

According to the invention, the model constructed from the database can operate in a succession of operations described hereafter.

In general, the fluid of unknown composition is likely to comprise several phases. For example, the fluid is a petroleum effluent comprising water, oil and gas.

The composition of the fluid located in a section T is determined using the family of values representing the modifications of the wave beam that has traversed the fluid of unknown composition in a section T, and possibly salinity, pressure and/or temperature values.

Operation 1

In the first place, the families of values of the database are classified in one of the "single-phase" categories or in the "mixture" category. Each "single-phase" category groups together the families of values characterizing a fluid consisting of a given single phase. There are as many "single-phase" categories as there are different phases likely to make up the fluid of unknown composition. The "mixture" category groups the families of values characterizing a fluid consisting of several phases, for example an emulsion of two or three phases.

Classification can be performed by means of a discriminant analysis that can be of linear, quadratic or neural network type.

If the model classifies the family of values characterizing the fluid of unknown composition in one of the "single-phase" categories, then the composition of the fluid of section T is clearly identified: the fluid consists a hundred per cent of the phase corresponding to the "single-phase" category assigned.

If the model classifies the family of values in the "mixture" category, then Operations 2 and 3 are carried out.

If fluid 7 is a petroleum effluent, the families of values of the database are classified in the following four categories: "water", "oil", "gas" and "mixture".

From this classification, the model classifies, by discriminant analysis, the family of values representing the modifications of the wave beam that has traversed the fluid of unknown composition in a section T in one of the categories.

If the family is classified in the "water" category, then the following composition is assigned to the fluid of section T: 100% water, 0% oil and 0% gas.

If the family is classified in the "oil" category, then the following composition is assigned to the fluid of section T: 0% water, 100% oil and 0% gas.

If the family is classified in the "gas" category, then the following composition is assigned to the fluid of section T: 0% water, 0% oil and 100% gas.

If the family is classified in the "mixture" category, operations 2 and 3 described hereafter are carried out to determine the composition of the fluid.

In operations 2 and 3, a family of values that has been classified in the "mixture" category is processed, i.e. the family of values characterizes a fluid comprising at least two different phases.

The proportion of the various phases can be estimated by means of a regression on the interval 0% to 100% for each phase. In order to improve the reliability of the model, the present invention proposes to split the interval [0%; 100%] into at least two intervals (Operation 2) and a regression is carried out interval by interval (Operation 3).

Operation 2

The families of values classified in the "mixture" category correspond to multiphase mixtures comprising phases in proportions ranging between 0% and 100%. These families of values are classified in subcategories. Each subcategory groups together the families that correspond to a fluid comprising a phase in a proportion contained in a fixed interval within [0%; 100%]. Preferably, for each phase, there are at least two subcategories whose intervals do not overlap and whose intervals cover in total the range [0%; 100%]. Thus, for each phase, the families of values are classified in one of the subcategories corresponding to a fixed proportion interval.

Classification can be performed by means of a discriminant analysis that can be of linear, quadratic or neural network type.

The discriminant analysis model allowing to assign one of the subcategories to a family of values characterizing a fluid of unknown composition is constructed from the classification in subcategories. In other words, the model indicates, for each phase, to which subcategory the family of values characterizing a fluid of unknown composition belongs. The model can be of linear, quadratic or neural network type.

If fluid 7 is a petroleum effluent, the families of values are classified in the "mixture" category, for example, in one of the following segments:

the subcategory corresponding to a proportion of water ranging between 0% and 30%, the subcategory corresponding to a proportion of water ranging between 30% and 70%, the subcategory corresponding to a proportion of water ranging between 70% and 100%, the subcategory corresponding to a proportion of oil ranging between 0% and 30%, the subcategory corresponding to a proportion of oil ranging between 30% and 70%, the subcategory corresponding to a proportion of oil ranging between 70% and 100%.

From this classification, a discriminant analysis submodel classifies the family of values representing the modifications of the wave beam that has traversed the petroleum effluent in a section T in one of the subcategories giving the proportion of water and in one of the subcategories giving the proportion of oil.

Operation 3

When the family of values representing the modifications of the wave beam that has traversed the fluid of unknown composition in a section T is classified in one of the subcategories, the proportion of the phase corresponding to this subcategory is determined by carrying out a regression on the interval corresponding to this subcategory. The regression can be of linear, PLS or neural network type.

For example, if the family of values representing the modifications of the wave beam that has traversed the petroleum effluent in a section T has been classified in the subcategory corresponding to a proportion of water ranging between 0% and 30%, and in the subcategory corresponding to a proportion of oil ranging between 70% and 100%, the proportion of water is determined by means of a regression on the 0% to 30% interval, and the proportion of oil is determined by means of a regression on the 70% to 100% interval.

Stage G: Determination of the Position of the Fluid Layers

In the application to a stratified fluid as illustrated in FIG. 3, the position of the various fluid layers is determined knowing the geometry of the sections T defined in stage C and knowing the composition, determined in stage C, of the fluid located in each section.

With reference to FIG. 7, the total volume of the fluid studied is divided into sections T. Sections T are defined by volumes located between horizontal planes, the sections being superposed. The position of the various fluid layers can thus be determined as a function of the height. The larger the number of sections, the higher the accuracy of the fluid layer position.

Repeating stages E, F and G allows to monitor the evolution with time of the position of the layers if the fluid is a stratified fluid. Monitoring can be carried out in real time and displayed visually.

After determining the positions of the fluid layers, the composition of the fluid making up each layer is determined. To determine the composition of the fluid making up a layer, stages B, C and D are carried out by taking into account only the beams that have travelled a path located in this layer only.

The invention claimed is:

1. A method for determining the composition of a substantially homogeneous fluid, wherein the following stages are carried out:
   a) measuring the attenuation and the phase shift of at least two wave beams that have travelled paths of different distances in said fluid;
   b) determining relations modelling the variations of the attenuation and phase shift of the waves as a function of the distance, measured in stage a); and
   c) determining the composition of the fluid by comparing the relations determined in stage b) with a set of previously determined relations, each relation of said set corresponding to a fluid of known composition.

2. A method as claimed in claim 1, wherein in stage a), the attenuation and the phase shift of more than two wave beams are measured, including at least two wave beams that have travelled two different paths of equal distance in said fluid and wherein a mean of the attenuations and of the phase shift measured for said at least two beams that have travelled two different paths of equal distance in said fluid is worked out.

3. A method as claimed in claim 2, wherein said mean is a weighted mean.

4. A method as claimed in claim 1, wherein in stage c), the set of previously determined relations is obtained by carrying out stages a) and b) on fluids of known composition.

5. A method as claimed in claim 1, wherein in stage b), a first equation of the attenuation as a function of the distance and a second equation of the phase shift as a function of the distance are determined, the first and second equations approaching the attenuation and phase shift measurements of stage a), and wherein in stage c), the composition of the fluid is determined by comparing the first and second equations determined in stage b) with pairs of previously determined equations, each pair of equations corresponding to a fluid of known composition.

6. A method as claimed in claim 5, wherein in stage b), said first equation is of the form $\rho = e^{-\alpha\theta - \alpha_0}$, said second equation is of the form $\theta = \lambda d + \lambda_0$, $\rho$ being the attenuation, $\theta$ being the phase shift, $\alpha, \alpha_0, \lambda$ and $\lambda_0$ being constants, and wherein the values of constants $\alpha, \alpha_0, \lambda$ and $\lambda_0$ are determined, and wherein in stage c), the values of the constants determined in stage b) are compared with groups of previously determined constants, each group of constants corresponding to a fluid of known composition, said groups of previously determined constants being obtained by carrying out stages a) and b) on fluids of known composition.

7. A method as claimed in claim 6, wherein in stage b), linear regression is used to determine the values of the constants.

8. A method as claimed in claim 1, wherein in stage c), at least one of the following conditions pressure of said fluid, temperature of said fluid and salinity of said fluid, is taken into account.

9. A method as claimed in claim 1, wherein in stage c), the composition of the fluid is determined by selecting in the set of previously determined relations those which best match the relations obtained in stage b).

10. A method as claimed in claim 1, wherein in stage c), a model allowing to assign a known composition to relations modelling the variations of the attenuation and phase shift as a function of the distance is used, the model being constructed by means of the set of previously determined relations.

11. A method as claimed in claim 10, wherein said model is a statistical model or a behavioural model, the model being a polynomial function or a neural network.

12. A method as claimed in claim 1, wherein said wave beams are microwave beams.

13. A method for determining the composition of a fluid contained in a volume, said fluid comprising at least two phases in stratified layers, wherein the following stages are carried out:
   a) defining several sections that divide said volume, each section comprising a part of said fluid;
   b) measuring the attenuation and the phase shift of a microwave beam that has travelled a path in a first one of said sections;
   c) determining the composition of the part of said fluid located in said first section by comparing the attenuation and the phase shift measured in stage b) with a set of pairs of previously determined attenuation and phase shift values, each pair of said set characterizing a fluid of known composition;
   d) repeating stages b) and c) for each section defined in stage a);
   e) determining the position of said layers from the compositions determined in stage c) and from the definition of the sections in stage a);
   f) measuring the attenuation and the phase shift of at least two wave beams that have travelled paths of different distances in a first one of said layers;
   g) determining relations modelling the wave attenuation and phase shift variations as a function of the distance, measured in stage f); and
   h) determining the composition of the fluid forming the first layer by comparing the relations determined in stage g) with a set of previously determined relations, each relation of said set corresponding to a fluid of known composition.

14. A method as claimed in claim 13, wherein the sections defined in stage a) are superposed and separated by parallel planes.

15. A method as claimed in claim 13, wherein in stage c), at least one of the following conditions pressure, temperature and salinity of said fluid, is taken into account.

16. A method as claimed in claim 13, wherein in stage c), a model allowing to assign a composition to a family of values measured in stage b) is used, the model being constructed from said set of families of values.

17. A method as claimed in claim 16, wherein a statistical model or a behavioural model of linear, quadratic and neural network type is used, and a regression of linear, PLS or neural network type is used.

18. A method as claimed in claim 17, wherein the fluid is a petroleum effluent comprising water, oil and gas, and wherein the model carries out operation 1: the family of values is classified by discriminant analysis in one of the following categories: water single-phase, oil single-phase, gas single-phase or multiphase,
   if the family of values is classified in a single-phase category, then the composition of the effluent is determined,
   if the family of values is classified in the multiphase category, operations 2 and 3 are carried out:
   Operation 2: the family of values is classified in a sub-category corresponding to a fluid comprising a phase in a proportion contained in a fixed interval within [0%; 100%], Operation 3: the proportion of the phase corresponding to the subcategory is determined by regression on the fixed interval.

19. A method for determining the composition of at least one layer of a fluid, wherein the following stages are carried out:
   d) measuring the attenuation and the phase shift of at least two wave beams that have travelled paths of different distances in at least said one layer of said fluid;
   e) determining relations modelling the variations of the attenuation and phase shift of the waves as a function of the distance, measured in stage a); and
   f) determining the composition of at least said one layer of said fluid by comparing the relations determined in stage b) with a set of previously determined relations, each relation of said set corresponding to a fluid of known composition.

* * * * *